United States Patent
Xu et al.

(10) Patent No.: US 11,369,657 B2
(45) Date of Patent: *Jun. 28, 2022

(54) SMALL MOLECULE POLYPEPTIDE FOR PREVENTING AND RESTRAINING INFLAMMATION AND APPLICATION OF SAME

(71) Applicants: SHANGHAI FIRST PEOPLE'S HOSPITAL, Shanghai (CN); Xun Xu, Shanghai (CN); Yan Xu, Shanghai (CN)

(72) Inventors: Xun Xu, Shanghai (CN); Yan Xu, Shanghai (CN); Qiao Sun, Shanghai (CN)

(73) Assignees: SHANGHAI FIRST PEOPLE'S HOSPITAL, Shanghai (CN); Xun Xu, Shanghai (CN); Yan Xu, Shanghai (CN)

( * ) Notice: Subject to any disclaimer, the term of this patent is extended or adjusted under 35 U.S.C. 154(b) by 470 days.

This patent is subject to a terminal disclaimer.

(21) Appl. No.: 15/633,296

(22) Filed: Jun. 26, 2017

(65) Prior Publication Data
US 2017/0360871 A1 Dec. 21, 2017

Related U.S. Application Data

(63) Continuation-in-part of application No. 14/412,497, filed as application No. PCT/CN2011/084246 on Dec. 19, 2011, now Pat. No. 9,688,726.

(51) Int. Cl.
| | | |
|---|---|---|
| *A61K 38/03* | (2006.01) | |
| *C07K 14/00* | (2006.01) | |
| *C07K 14/47* | (2006.01) | |
| *A61K 38/00* | (2006.01) | |

(52) U.S. Cl.
CPC .............. *A61K 38/03* (2013.01); *C07K 14/00* (2013.01); *C07K 14/4702* (2013.01); *A61K 38/00* (2013.01)

(58) Field of Classification Search
CPC ..... C07K 14/00; C07K 14/4702; A61P 37/00; A61P 31/00; A61K 38/00; A61K 38/03
See application file for complete search history.

(56) References Cited

U.S. PATENT DOCUMENTS 7,041,491 B2 5/2006 Inohara et al.

FOREIGN PATENT DOCUMENTS

| CN | 102037006 | 4/2011 |
| WO | 01/57261 | 8/2001 |
| WO | 2009/090168 | 7/2009 |

OTHER PUBLICATIONS

Luck, D.N., Single amino acid substitutions in recombinant bovine prolactin that markedy reduce its mitogenic activity in Nb2 cell cultures. Molecular Endocrinology, 1991, 5:1880-1886.*
Pakula, A.A., et al. Genetic analysis of protein stability and function. Annual Reviews of Genetics. 1989, 23:289-310.*
Robey, E.A., Effect of amino acid substitutions on the catalytic and regulatory properties of aspartate transcarbamoylase. Proc. Natl. Acad. Sci. USA, 1986, 83:5934-5938.*
Sitbon, M, et al. Substitution of leucine for isoleucine in a sequence highly conserved among retroviral envelope surface glycoproteins attenuates the lytic effect of the Friend murine leukemia virus. Proc. Natl. Acad. Sci. USA., 1991, 88:5932-5936.*
Azzam, S.H., et al. Tocilizumab for thyroid eye disease (Review), Cochrane Database of Systemic Reviews, 2018, Issue 11, Art. No. CD12984, p. 1-18).*
Chudy-Onwugaje, K.O., et al. A state-of-the-art review of new and emerging therapies for the treatment of IBD. Inflamm. Bowel. Dis., 2019, 25(5):820-830.*
Sbidian, E., et al. Systemic pharmacological treatments for chronic plaque psoriasis: a nework meta-analysis (Review), Cochrane Database of Systemic Reviews, 2017, Issue 12, Art. No. CD011535, p. 1-499.*
International Search Report for international application No. PCT/CN2011/084246, dated Aug. 16, 2012 (8 pages).
Genbank Accession No. EAW82900, version EAW82900.1; retrieved from Genbank database (www.ncbi.nlm.nih.gov) dated Dec. 18, 2006 (6 pages).
S. Benko et al., "NLRC5 limits the activation of inflammatory pathways," J. Immunol., 2010, vol. 185, p. 1681-1691.
J.E. Mickle at al., "Genotype-phenotype relationships in cystic fibrosis," Medical Clinics of North America, 2000, vol. 84, No. 3, p. 597-607.
J.A. Wells, "Additivity of mutational effects in proteins," Biochemistry, 1990, vol. 29, No. 37, p. 8509-8517.

* cited by examiner

*Primary Examiner* — Prema M Mertz
(74) *Attorney, Agent, or Firm* — Hamre, Schumann, Mueller & Larson, P.C.

(57) ABSTRACT

The present invention provides a polypeptide that is rich in leucine and used for preventing and restraining inflammation, and an application of same. The present invention further provides a method for preparing the polypeptide and a pharmaceutical composition containing the polypeptide. The advantage of the polypeptide comprises: small molecular weight, so as to permeate various eye tissue barriers; high water solubility, so as to have high dissolubility in neutral tears, aqueous humor and vitreous humor; and simple synthesis, so as to have a low preparation cost.

7 Claims, 5 Drawing Sheets

Specification includes a Sequence Listing.

a b

SMALL MOLECULE POLYPEPTIDE FOR PREVENTING AND RESTRAINING INFLAMMATION AND APPLICATION OF SAME

INCORPORATION BY REFERENCE MATERIAL IN ASCII TEXT FILE

This application incorporates by reference the Sequence Listing contained in the following ASCII text file being submitted herewith:
a) Filename: Sequence_Listing.txt_0051, created Jun. 26, 2017, 7.89 KB in size.

REFERENCE TO A "SEQUENCE LISTING"

The sequence listing submitted via EFS, in compliance with 37 CFR § 1.52(e)(5), is incorporated herein by reference. The sequence listing text file submitted via EFS contains the file "Substitute Sequence Listing.txt", created on Dec. 13, 2019, which is 9.53 KB in size.

TECHNICAL FIELD

The present invention relates to the bio-pharmaceutical filed. Specifically, the present invention related to a small molecule polypeptide for preventing and inhibiting inflammation and the use thereof. The present invention further relates to a preparation method and use of said polypeptide, and a pharmaceutical composition comprising the polypeptide.

BACKGROUND

Inflammation is a natural reaction of living organisms to external factors, such as infection, trauma, etc., which damage their tissues and cells, and varies types of cells, mediums, and stimulators are involved. Acute inflammation is a short-term reaction, which will generally promote the organism to heal. On the contrary, chronic inflammation is an adverse reaction with protracted disfunction. In fact, chronic inflammation involves many systemic and local pathological states and pathogenesis of the living organisms, wherein the former is, such as brain nerve disfunction, diabetes, hepatitis, rheumatoid arthritis and tumors in different part of the body, and the latter is, such as uveitis, keratitis etc.

Epidemiological investigation showed that the incidence and morbidity of uveitis, as one of the major blinding diseases, is increased. In US and Europe, uveitis accounts for about 5-20% of blinding diseases, while the number goes up to about 25% in developing countries. Uveitis has caught the attention from ophthalmology field in the world since it mainly affect the young adults, is hard to treat and prone to recur, and may cause blind if not being timely or proper treated.

Autoimmune disease and infection are the main pathogenic factors for uveitis. When the organism is infected, the macrophages in the body are activated by bacterial toxin (eg. lipopolysaccharide), thereby inducing the secretion of a series of inflammation-related cytokines and chemokines, such as tumor necrosis factor (TNF)-α, interleukin (IL)-6, (MCP)-1, etc., and these inflammatory factors are essential to many chronic inflammatory diseases.

For a long time, corticosteroid hormones have been the best choice for treating uveitis. Especially for treating obstinate uveitis, long-term medication is needed for preventing its recurrence. However, there are many potential side effects for corticosteroid hormone, such as intraocular hypertension, cataract, infection, delayed wound healing, etc., thus limiting the clinical application of the medicine. Immunosuppressors, such as cyclosporine A, FK506, etc., are the second-line medicine for inhibiting inflammation, and also have severe side effects such as liver and kidney injury. At present, some therapeutic effects have been achieved by using biological agents such as monoclonal antibodies (eg. anti-TNF agents and IL receptor antagonist, lymphocytes activation inhibiting agents, immunoregulating and anti inflammatory cytokines agents, etc.) to inhibit or block disease-related lymphocytes, cytokines or cytokine receptors. However, the biological agents belong to macromolecule proteins, therefore they are hard to synthesize and too expensive to be clinically promoted. Besides, the specificity of ocular agents should be sufficiently considered in developing effective anti-inflammation agents.

Firstly, many effective macromolecule antagonists are weaken or failed to reach intraocular focus due to the existence of several anatomic and physiological barriers in the eye balls. In the case of commonly used ocular surface administration route, the agents have to successively penetrate the lipophilic tight junctions between corneal epithelial cells and then the hydrophilic corneal stroma. Thus, only the agents with appropriate lipophilicity, low molecular weight or the capability of binding with the transporters in ocular surface tissues can reach the anterior chamber and function effectively. The agent concentration reached in the eyes will be greatly reduced due to the blood-aqueous barrier in iris and blood-retina barrier in retina-choroid if the agents are administered orally.

Secondly, the solubility of the drugs in the hydrophilic tears, aqueous humor, and vitreous humor is positively correlated to their effectiveness.

Finally, the bioavailability of ocular agents is very low. The administration concentration must be increased to improve the bioavailability.

Therefore, there is an urgent need to develop a small molecule anti-inflammation agent which is suitable for eye ball tissues, safe and effective.

SUMMARY OF INVENTION

The object of the invention is to provide a small molecule polypeptide and the fragment, analogue and derivative thereof, which are suitable for eye ball tissues, safe and effective for inhibiting inflammation reaction.

Another object of the present invention is to provide preparation methods and uses of said polypeptides.

In the first aspect, the present invention provides a polypeptide of Formula I, or a pharmaceutically acceptable salt thereof (I)
[Xaa0]-[Xaa1]-[Xaa2]-[Xaa3]-[Xaa4]-[Xaa5]-[Xaa6]-

[Xaa7]-[Xaa8] [Xaa9]-[Xaa10]-[Xaa11]-[Xaa12]-

[Xaa13]-[Xaa14]-[Xaa15]-[Xaa16]-[Xaa17]-[Xaa18]-

[Xaa19]-[Xaa20]-[Xaa21]-[Xaa22]-[Xaa23]

wherein,

Xaa0 is absent, or a peptide segment consisting of 1-3 amino acids;

Xaa1 is selected from the group consisting of Leu, Ile, Val, Met, Ala and Phe;

Xaa2 is selected from the group consisting of Asp, Glu, Cys and Ser;

Xaa3 is selected from the group consisting of Leu, Ile, Val, Met, Ala and Phe;

Xaa4 is selected from the group consisting of Ser and Thr;

Xaa5 is selected from the group consisting of His, Arg, Gl, Lys, Arg, Glu and Asp;

Xaa6 is selected from the group consisting of Asn, Gln, His, Thr, Ser, Lys, Arg, Cys and Ser;

Xaa7 is selected from the group consisting of Ser, Thr, Pro and Ala;

Xaa8 is selected from the group consisting of Ile, Leu, Val, Met, Ala and Phe;

Xaa9 is selected from the group consisting of Ser, Thr, Glu and Asp;

Xaa10 is selected from the group consisting of Gln, Asn, Pro and Ala;

Xaa11 is selected from the group consisting of Glu, Asp, Pro and Ala;

Xaa12 is selected from the group consisting of Ser and Thr;

Xaa13 is selected from the group consisting of Ala, Val, Leu and Ile;

Xaa14 is selected from the group consisting of Leu, Ile, Val, Met, Ala, Phe, Thr and Ser;

Xaa15 is selected from the group consisting of Tyr, Trp, Phe, Thr, Ser, Lys, Gln and Asn;

Xaa16 is selected from the group consisting of Leu, Ile, Val, Met, Ala and Phe;

Xaa17 is selected from the group consisting of Leu, Ile, Val, Met, Ala, Phe, Cys and Ser;

Xaa18 is selected from the group consisting of Glu, Asp, Ala, Val and Ile;

Xaa19 is selected from the group consisting of Thr and Ser;

Xaa20 is selected from the group consisting of Leu, Ile, Val, Met, Ala and Phe;

Xaa21 is selected from the group consisting of Pro, Ala, Lys and Arg;

Xaa22 is selected from the group consisting of Ser, Thr, Asp and Glu;

Xaa23 is absent, or a peptide segment consisting of 1-3 amino acids; and the polypeptide exhibits an activity of inhibiting inflammation reaction.

In another preferred embodiment, the polypeptide is 22-25 amino acids in length.

In another preferred embodiment, Xaa0 and Xaa23 are absent.

In another preferred embodiment, Xaa0 or Xaa23 is a segment consisting of 1-3 amino acids.

In another preferred embodiment, Xaa0 is selected from the group consisting of W, RK, K, LHQ, HQ and Q.

In another preferred embodiment, Xaa23 is selected from the group consisting of R, RA, and RAK.

In another preferred embodiment, the polypeptide is selected from the group consisting of:

(a) a polypeptide having the amino acid sequence of SEQ ID NO.: 1;

(b) a polypeptide which is derived from the polypeptide of (a) by substitution, deletion, or addition of 1-5 amino acids to the amino acid sequence of SEQ ID NO: 1 and which has the activity of inhibiting inflammation.

In another preferred embodiment, the polypeptide is a polypeptide which is derived from the polypeptide of (a) by substitution of 1-5, preferably 1-3, more preferably 1 amino acid to the amino acid sequence of SEQ ID NO: 1 with Ala and which has the activity of inhibiting inflammation.

In another preferred embodiment, the polypeptide is:

Polypeptide 8 (SEQ ID NO.: 11): the sequence of which is the same as SEQ ID NO.: 1 except that Asn in Xaa6 is substituted by Ala, or Polypeptide 9 (SEQ ID NO.: 12): the sequence of which is the same as SEQ ID NO.: 1 except that Glu in Xaa11 is substituted by Ala, or Polypeptide 10 (SEQ ID NO.: 13): the sequence of which is the same as SEQ ID NO.: 1 except that Glu in Xaa18 is substituted by Ala, or Polypeptide 11 (SEQ ID NO.: 14): the sequence of which is the same as SEQ ID NO.: 1 except that Thr in Xaa19 is substituted by Ala, or Polypeptide 12 (SEQ ID NO.: 15): the sequence of which is the same as SEQ ID NO.: 1 except that Leu in Xaa20 is substituted by Ala, or Polypeptide 13 (SEQ ID NO.: 16): the sequence of which is the same as SEQ ID NO.: 1 except that Pro in Xaa21 is substituted by Ala, or Polypeptide 14 (SEQ ID NO.: 17): the sequence of which is the same as SEQ ID NO.: 1 except that Ser in Xaa22 is substituted by Ala, or Polypeptide 15 (SEQ ID NO.: 18): the sequence of which is the same as SEQ ID NO.: 1 except that Leu in Xaa1 is substituted by Ala, or Polypeptide 16 (SEQ ID NO.: 19): the sequence of which is the same as SEQ ID NO.: 1 except that Asp in Xaa2 is substituted by Ala, or Polypeptide 17 (SEQ ID NO.: 20): the sequence of which is the same as SEQ ID NO.: 1 except that Leu in Xaa3 is substituted by Ala, or Polypeptide 18 (SEQ ID NO.: 21): the sequence of which is the same as SEQ ID NO.: 1 except that Ser in Xaa4 is substituted by Ala, or Polypeptide 19 (SEQ ID NO.: 22): the sequence of which is the same as SEQ ID NO.: 1 except that Ser in Xaa7 is substituted by Ala, or Polypeptide 20 (SEQ ID NO.: 23): the sequence of which is the same as SEQ ID NO.: 1 except that Ser in Xaa9 is substituted by Ala, or Polypeptide 21 (SEQ ID NO.: 24): the sequence of which is the same as SEQ ID NO.: 1 except that Ser in Xaa12 is substituted by Ala, or Polypeptide 22 (SEQ ID NO.: 25): the sequence of which is the same as SEQ ID NO.: 1 except that Leu in Xaa16 is substituted by Ala, or Polypeptide 23 (SEQ ID NO.: 26): the sequence of which is the same as SEQ ID NO.: 1 except that Leu in Xaa17 is substituted by Ala.

In another preferred embodiment, the polypeptide further includes a polypeptide which is derived from the amino acid sequence of SEQ ID NO.: 1 by modification according to the amino acid sequence in NLRC5 protein from the species besides human, and which has the activity of inhibiting inflammation.

In another preferred embodiment, said derived polypeptide retains ≥70% (preferably ≥80%; and more preferably ≥90%) activity of inhibiting inflammation-immune reaction of the polypeptide of SEQ ID NO.: 1.

In another preferred embodiment, the homology between said derived polypeptide and the sequence of SEQ ID No.: 1 is ≥80%, preferably ≥90%; and more preferably ≥95%.

In the second aspect, the present invention provides dimer and polymer form of the compound of formula I (or the derived polypeptide thereof), which exhibit the activity of inhibiting inflammation-immune reaction.

In the third aspect, the present invention provides another polypeptide having the activity of inhibiting inflammation, which are selected from:

(a) a polypeptide having the amino acid sequence of SEQ ID NO.: 3 or 5;

(b) a polypeptide which is derived from the polypeptide of (a) by substitution, deletion, or addition of 1-5 amino acids to the amino acid sequence of SEQ ID NO: 3 or 5 and which has the activity of inhibiting inflammation.

In the fourth aspect, the present invention provides an isolated nucleic acid molecule encoding the polypeptide according to the first or the third aspect of the present invention.

In the fifth aspect, the present invention provides a pharmaceutical composition comprising:

(a) the polypeptide according to the first or the third aspect of the present invention or a pharmaceutically acceptable salt thereof; and (b) a pharmaceutically acceptable carrier or excipient.

In another preferred embodiment, said pharmaceutical composition further comprises: (iii) a pharmaceutically acceptable anti-inflammatory or immunosuppresive medicament.

In another preferred embodiment, said anti-inflammatory or immunosuppresive medicament is selected from the group consisting of corticosteroid drugs, such as prednisone, dexamethasone, beclomethasone, etc.; non-steroidal anti-inflammatory drugs, such as salicylic acid, ibuprofen, celecoxib and rofecoxib, etc.; immunosuppresants, such as cyclophosphamide, azathioprine, mycophenolate mofetil, etc.

In another preferred embodiment, said composition is in the form of eyedrop, injection, or eye ointment.

In another preferred embodiment, said composition is in a slow-release dosage form.

In another preferred embodiment, said injection is a retrobulbar and intraocular injection liquid.

In the sixth aspect, the present invention provides a use of the polypeptide or a pharmaceutically acceptable salt thereof according to the first or the third aspect of the invention: (a) for preparing medicaments for inhibiting inflammation-immune reaction or treating inflammation-immune reaction related diseases; (b) for preparing inhibitors for inflammatory factors; or (c) for preparing anti-infective medicaments.

In another preferred embodiment, said inflammatory factor is TNF-α or cytokine; and more preferably, said cytokine is IL-6.

In another preferred embodiment, said inflammation related disease is selected from the group consisting of autoimmune ophthalmopathy, inflammatory ophthalmopathy, rheumatoid arthritis, juvenile rheumatoid arthritis, seronegative spondyloarthritis, psoriatic arthritis, psoriasis and inflammatory bowel disease.

In another preferred embodiment, said autoimmune ophthalmopathy includes: various of keratoconjunctivitis, iris and ciliary body inflammation, intermediate uveitis, posterior uveitis, scleritis, retinal choroidal inflammation, proliferative vitreoretinopathy; diseases with inflammatory factors involved in pathogenesis, including diabetic retinopathy disease and age-related macular degeneration, etc.

In the seventh aspect, the present invention provides a method for inhibiting inflammation in mammals, comprising the step of administering the polypeptide according to the first or the third aspect of the present invention to a subject in need thereof.

In another preferred embodiment, the subject is human.

In another preferred embodiment, the inflammation reaction is uveitis related inflammation reaction.

In the eighth aspect, the present invention provides a method for preparing a pharmaceutical composition, comprising the step of mixing (i) the polypeptides or a pharmaceutically acceptable salt thereof according to the first or the third aspect of the present invention with (ii) a pharmaceutically acceptable carrier or excipient, thereby obtaining the pharmaceutical composition.

It should be understood that in the present invention, the technical features specifically described above and below (such as the Examples) can be combined with each other, thereby constituting a new or preferred technical solution which needs not be described one by one.

DESCRIPTION OF DRAWINGS

The following drawings are to illustrate the specific embodiments of the present invention. They should not be construed as limiting the scope of the present invention, which should be defined by the claims.

FIG. 1 shows the identification results of LS22 in Example 1, wherein, FIG. 1a is a HPLC pattern and FIG. 1b is a MS pattern.

FIG. 2a shows that the count of exuded cells in rat anterior chamber is remarkably increased 24 hours after LPS is injected compared with blank control group, while the count of exuded cells is remarkably reduced in LS22 group. FIG. 2b shows that protein concentration in rat aqueous fluid is remarkably increased 24 hours after LPS is injected compared with blank control group, while protein concentration in aqueous fluid is remarkably decreased in LS22 group. The results of histopathologic examination in FIG. 2c shows that massive amounts of cells are exuded into the rat anterior chamber, ciliary body, and posterior vitreous cavity after LPS is injected. FIG. 2d shows that the amounts of inflammatory cells in tissues are greatly reduced by LS22 intervention and the anti-inflammatory action is significant.

FIG. 3a shows that compared with blank control group, TNF-α level is greatly increased in cell supernatant in LPS group, while the LPS induced TNF-α level is significantly inhibited in LS22 group. FIG. 3b shows that compared with blank control group, IL-6 level is greatly increased in cell supernatant in LPS group, while LPS induced IL-6 level is significantly inhibited in LS22 group.

DETAILED DESCRIPTION OF THE INVENTION

Figure 1:
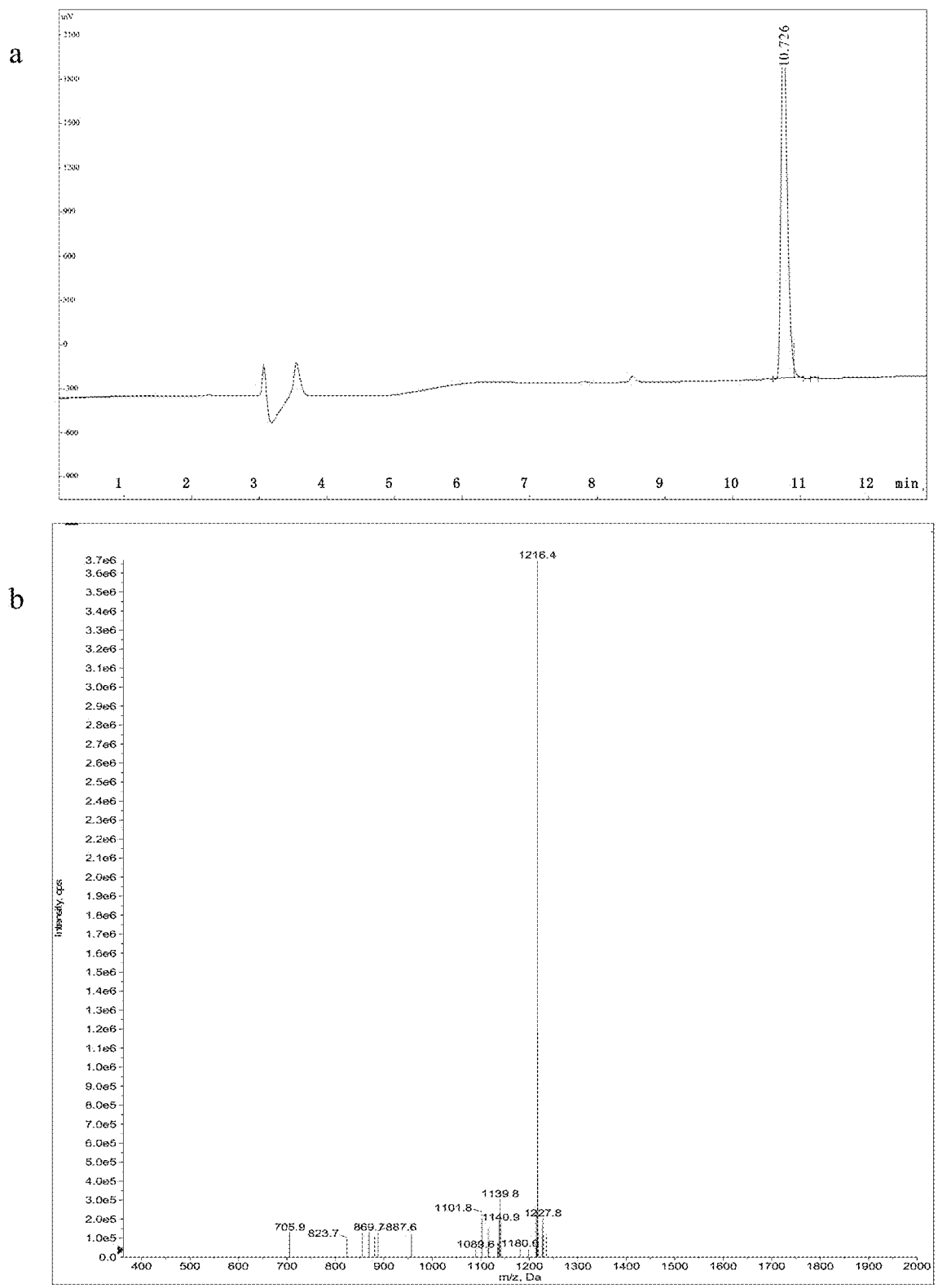

After extensive and intensive studies, the inventors have firstly prepared a class of small molecular polypeptides with a molecular weight of less than 3 kD (for example, only about 2.4 KD) which are derived from NLRC5 protein, and exhibit a function of inhibiting inflammation. In particular, by utilizing the method of bioinformatics, the inventor designed several candidate sequences derived from NLRC5 protein based on the homology analysis and analysis on the biological properties. Small peptides with high purity were obtained through solid-phase synthesis, separation and purification, and then subjected to HPLC and MS identification. Upon further screening through the model of uveitis and the model of rat macrophage proliferation induced by LPS, a novel class of small molecular polypeptides exhibiting the function of anti-inflammation was obtained.

Due to the low molecular weight, the small peptides of the present invention can penetrate through various ocular tissue barriers and have good water solubility so that they can maintain a relatively high concentration in neutral tears, aqueous humor and vitreous humor. They are highly safe with a minor toxicity or side-effect to the biological tissue. The bioavailability in eye topical administration is high, thus the dose can be reduced, and hence the systemic toxicity can also be reduced. Based on the above work, the inventors finish the present invention.

NLRC5 and LRR

NLRC5 protein belongs to the nucleotide-binding oligomerization domain like receptor (NLR) family and consists of a caspase recruitment domain (CARD), a nucleotide-binding oligomerization domain (NOD) and a leucine-rich repeats domain (LRR). Leucine-rich repeat sequence was firstly discovered in leucine-rich a2 glycoprotein and then named. It has been found that LRRs widely exist in virus, yeast and varies tissues of mammals. The functions of most LRRs proteins are associated with the interaction between protein ligands. Most LRRs are 20-30 amino acids in length with 2-52 repeats. These LRR proteins are divided into 7 sub-families. Each LRR sequence comprises highly conserved sequence and variable area. The highly conserved sequence consists of 11 amino acids (LxxLxLxxNxL) or 12 amino acids (LxxLxLxxCxxL) frame, which formed into a short β-sheet. Among these conserved sequences, "L" is Leu, Ile, Val or Phe, "N" is Asn, Thr, Ser, or Cys, and "C" is Cys or Ser.

For the proteins containing LRRs sequences, NLRs represent a PRRs family in a cell and are characterized in that it comprises conserved nucleotide-binding oligomerization domain (NOD) and Leucine-rich repeats domain (LRR) and their function are associated with the activation of many signal pathways. NLRs family proteins (eg. NOD1, NOD2, NLRX1 and NALP3) have been proved to induce the transduction of signal pathways once certain pathogen-associated molecular patterns (PAMP) occur.

Active Polypeptides

LS22 polypeptide is derived from NLRC5, one of the nucleotide-binding oligomerization domain receptor (NLR) family. In the present invention, the terms "the polypeptide(s) of the present invention", "LS22 polypeptide(s)", "LS22 small peptide(s)", or "peptide(s) LS22" are interchangeable and refer to a protein or polypeptide having peptide LS22 amino acid sequence (SEQ ID NO: 1) and exhibiting an activity of inhibiting inflammation. In addition, said terms comprise the variants of SEQ ID NO: 1 which exhibit the function of inhibiting inflammation. These variations include, but are not limited to, deletions, insertions and/or substitutions of 1-5 (typically 1-4, preferably 1-3, more preferably 1-2, most preferably 1) amino acids, and addition of one or more (typically less than 5, preferably less than 3, more preferably less than 2) amino acids at C-terminus and/or N-terminus. For example, a protein's functions are usually unchanged when an amino residue is substituted by another amino acid with similar or analogous properties in the art. For another example, generally, the structure and function of protein won't be changed by the addition of one or several amino acids at C-terminus and/or N-terminus. Furthermore, the terms also include the monomer and polymer of the polypeptide of the present invention. For example, the adjacent upstream residue(s) of SEQ ID NO.: 1 is (are) "W" (mouse) or LHQ (bovine).

The present invention further includes the active fragments, derivatives and analogs of LS22 protein. As used herein, the terms "fragments", "derivatives" and "analogs" refer to the polypeptides substantially maintaining the function or activity of inhibiting inflammation-immune reaction. The polypeptide fragments, derivatives or analogs of the present invention may be (i) a polypeptide with one or more conservative or non-conservative amino acid residues (preferably the conservative amino acid residues) being substituted, or (i) a polypeptide having substituted group(s) in one or more amino acid residues, or (111) a polypeptide formed by fusion of LS22 polypeptide with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6His. According to the teachings herein, these fragments, derivatives and analogs are within the scope commonly known by the skilled person.

A class of preferred active derivatives is the polypeptides formed by replacing at most 5, preferably at most 3, more preferably at most 2, most preferably 1 amino acid in the amino acid sequence of formula I with amino acids having similar or analogous properties. These conservative variant polypeptides are preferably formed by carrying out the amino acid replacement according to Table I.

TABLE I

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides analogues of LS22 polypeptide. These analogues can differ from naturally occurring LS22 polypeptide in amino acid sequence or in modifications that do not affect the sequence, or both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acelylation, or carboxylation. Also included is modification of glycosylation, e.g., the polypeptides produced through glycosylation modification during its synthesis and processing or in the further processing steps. These modifications can be conducted by exposing the polypeptide to glycosylation enzymes (e.g., mammalian glycosylation or deglycosylation enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salts derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals (such as sodium, potassium, calcium or magnesium), and esters, carbamate or other conventional "prodrug" forms.

Encoding Sequences

The present invention further relates to a polynucleotide encoding LS22 polypeptide. A preferred encoding sequence, which encodes short peptide of SEQ ID NO.: 1 or 3 respectively, is SEQ ID NO.: 2 or 4.

In another preferred embodiment, the polynucleotide of the present invention can be in a form of DNA or RNA. DNA can be the coding strand or the non-coding strand. The coding sequence encoding the mature polypeptide can be identical with the coding sequence indicated in SEQ ID NO: 2, or can be a degenerate variant thereof. As used herein, "degenerate variant" refers to a nucleic acid sequence which encodes the protein having the amino acid sequence of SEQ ID NO:1, but is different from the corresponding coding sequence in SEQ ID NO: 2; or to a nucleic acid sequence which encodes the protein having the amino acid sequence of SEQ ID NO:3, but is different from the corresponding coding sequence in SEQ ID NO: 4.

The full length of LS22 nucleotide sequence or fragment thereof of the present invention can be obtained via PCR amplification, recombinant method or artificial synthesis. Currently, the DNA sequence encoding the polypeptide (or fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell engineered by using the vector or the coding sequence of the LS22 polypeptide of the present invention.

In another aspect, the present invention further comprises polyclonal antibodies or monoclonal antibodies specific to polypeptides encoded by LS22 DNA or fragments thereof, especially the monoclonal antibodies.

Preparation Method

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

One preferred method is to use liquid phase synthesis technique or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylfomamide for 20 minutes at room temperature to remove the Fmoc protective groups. Then the sequence is extended one by one from the C-terminus to the N-terminus according to the predetermined amino acid sequence. After synthesis, trifluoroacetic acid containing 4% p-methylphenol is used to cleave the peptide from the resin and the protective groups are removed. The resin can be filtered off, and the crude peptide can be obtained via precipitation with ether. The solution of the resultant product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine (DIEA)/dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular sieve Sephadex G10 or Tsk-40f. Then the desired peptide is obtained via high pressure liquid purification. Various coupling agents and coupling methods known in the peptide chemistry can be used to couple each amino acid residue. For example, dicyclohexylcarbodiimide (DCC), hydroxylbenzotriazole (HOBt) or 1,1,3,3-tetramethyluronium Hexafluorophosphate (HBTU) can be used for direct coupling. The purity and structure of the resultant short peptide can be verified by reverse phase HPLC and mass spectrometry.

In a preferred embodiment, the polypeptide LS22 of the present invention is prepared by solid phase method according to its sequence, and purified by high performance liquid chromatography, thereby obtaining freeze-dried powder of target peptide with high purity. The powder is stored at −20° C.

Another method is to produce the polypeptide of the present invention by a recombinant technique. With the conventional recombinant DNA technique, the polynucleotide of the present invention can be used to express or produce recombinant LS22 polypeptides. Generally, the method comprises the following steps:

(1) Transforming or transducing a suitable host cell with a polynucleotide or variant thereof encoding the LS22 polypeptide of the present invention or a recombinant expression vector containing said polynucleotide;

(2) Culturing the host cell in a suitable culture medium;

(3) Isolating and purifying protein from the culture medium or cells.

The recombinant polypeptide may be expressed in the cells, or expressed on the cell membrane, or secreted out of the cell. If desired, the recombinant protein can be isolated and purified according to the physical, chemical and other properties thereof by various isolation methods. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and combinations thereof.

It is also contemplated to link multiple polypeptides of the present invention in series due to their short length. After recombinant expression, the expressed product is obtained and enzyme-cleaved to form the desired small peptides.

Pharmaceutical Composition and Methods of Administration

In another aspect, the present invention further provides a pharmaceutical composition, comprising (a) a safe and effective amount of the polypeptide of the present invention or a pharmaceutically acceptable salt thereof; (b) a pharmaceutically acceptable carrier or excipient; and (c) a mixed agents comprising a pharmaceutically acceptable anti-inflammatory or immunosuppressive medicament. The amount of the polypeptide of the present invention generally is 10 μg to 100 mg per dose, preferably 100-1000 μg per dose.

For the purpose of the invention, the effective dose is about 0.01 mg to 50 mg of the polypeptide of the present invention per kg body weight, preferably 0.05 mg to 10 mg of the polypeptide of the present invention per kg body weight administered to an individual. Further, the polypeptide of the present invention can be used alone, or in combination with other therapeutic agents (for example, formulated into the same pharmaceutical composition).

The pharmaceutical composition can further comprise a pharmaceutically acceptable carrier. The term "pharmaceutically acceptable carrier" refers to the carrier for using in administering the therapeutic agents. The term refers to such drug carriers that themselves do not induce antibody deleterious to the subject receiving the composition, and do not produce excessive toxicity upon administration. These carriers are well known by the skilled person in the art. The detailed discussion about pharmaceutically acceptable excipients can be found in Remington's Pharmaceutical Sciences (Mack Pub. Co., N.J., 1991). Such carriers include, but are not limited to, saline, buffer solution, glucose, water, glycerin, ethanol, adjuvant or combinations thereof.

The pharmaceutically acceptable carrier in the therapeutic composition can comprise liquid, such as water, saline, glycerin, and ethanol. Moreover, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulating the composition of the present invention, it can be administered via conventional routes which include, but are not limited to, administering intra-ocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include eyedrop, injection, ophthalmic gel, and eye ointment.

The pharmaceutical composition can be formulated by mixing, diluting or dissolving according to the conventional methods. And, occasionally, suitable medicine additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulation can be carried out in a conventional manner according to the dosage form.

For example, formulation of eyedrop can be prepared as follows: dissolving short peptide LS22 or a pharmaceutically acceptable salt thereof and the basic substances in sterile water (surfactant is dissolved in said water), adjusting osmotic pressure and alkalinity acidity to the physiological state, optionally adding suitable medicine additives, such as preservatives, stabilizing agents, buffering agents, isotonicities, anti-oxidants and tackifiers, and then allowing them completely dissolved.

The pharmaceutical composition of the present invention can further be administered in a form of slow release formulation. For example, the short peptide LS22 or a salt thereof can be incorporated into a pill or microcapsule in which a slow release polymer is used as carrier, and then the pill or microcapsule is implanted into the tissue to be treated by operation. Furthermore, the short peptide LS22 or a salt thereof can be used by insertion of intra-ocular lens pre-coated with said drugs. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples of the slow release polymer include the biodegradable polymers, such as polymer of lactic acid, and lactic acid-glycolic acid copolymer.

When the pharmaceutical composition of the present invention is used in the actual treatment, the dose of the short peptide LS22 or a pharmaceutically acceptable salt thereof, as an active ingredient, can be suitably determined according to the body weight, age, gender, symptom of each patient. For example, when topically dropping in the eye, the concentration of the active ingredient generally is 0.1-10 wt %, preferably 1-5 wt %, 2-6 times per day and 1-2 drops for each time.

INDUSTRIAL APPLICABILITY

The pharmaceutical composition containing the peptide of the present invention or a pharmaceutically acceptable salt thereof as an active ingredient exhibits significant inhibition activity on inflammation-immune reaction. As verified by animal tests, the polypeptides of the present invention can inhibit intraocular inflammation of experimental uveitis induced by LPS.

The Main Advantages of the Present Invention Include:

(a) The polypeptide of the present invention has low molecular weight, so that it can penetrate various of ocular tissue barriers.

(b) The polypeptide of the present invention has good water solubility, so that it can maintain relatively high concentration in neutral tears, aqueous humor and vitreous humor.

(c) The polypeptide of the present invention has high safety with less toxicity to the tissue of the organism.

(d) The polypeptide of the present invention can be prepared via solid phase synthesis with high purity, high yield and low cost.

Therefore, the polypeptide of the present invention can be developed into a medicine for treating inflammatory ophthalmopathy and related inflammatory diseases, such as rheumatism, uveitis, etc.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Synthesis, Separation and Identification of Small Peptide LS22

The small peptide (SEQ ID NO: 1) was synthesized by using the commercially available SYMPHONY polypeptide synthesizer (Protein Technologies, US) as the following steps:

1. The desired amino acids protective solution, condensation reagents, and cleavage reagents were calculated and prepared according to the software (Version.201), and sufficient DMF (15 ml/g) (Dikma), DCM were added into the corresponding flasks in the synthesizer.

2. 100 μmol of FMOC-Ala-Wang-Resin was added into the reactor.

3. A centrifuge tube (15 ml) was placed to the tunnel for collecting cleavage fluid.

4. The program was set as follows: typically, 30 min for resin swelling, 5 min and 15 min for deprotection respectively, 30 min for condensation, 2 h for cleavage program.

5. The synthesis was conducted as programmed.

6. Finally, the cleavage fluid was precipitated by ether, centrifuged, blow-dried and purified by HPLC. FIG. 1 shows the identification results of small peptide LS22, wherein, the purified result of HPLC is shown in FIG. 1a, and MS pattern is shown in FIG. 1b.

7. 120 mg of polypeptide LS22 was obtained as white powder with good water solubility (purification >95%) and then sealed and stored for use at −20° C.

Example 2

LS22 Inhibited Uveitis in Rats

1. Main Materials and Equipments 8-week old male wistar rats with the body weight of 160-220 g were purchased from Sino-Brithish SIPPR/BK; Whatman filter paper was purchased from Sigma; LPS (*Escherichia coli*, 055:B5 purchased from Sigma).

2. Model Construction and Intervention Experiment 8-week old male wistar rats were randomly divided into 5 groups with 10 rats for each, which are blank+PBS, LPS+PBS group, LPS+LS22 10 μg group, LPS+LS22 50 μg group, LPS+LS 22 100 μg group. 0.15 ml of pentobarbital (5.47 g/100 ml normal saline) was intraperitoneally injected into the rats for anesthesia. 100 μl of LPS (2 μg/μl) was subcutaneously injected into the right hindpaw of rats both in treating group and positive control group. An equal volume of normal saline was injected into the same position of the rats in blank+PBS group. 5% tropicamide and 1% tetracaine was dropped on the eye for mydriasis and local anesthesia. Under operating microscope, 10 μl of polypeptide or PBS of equal volume was intravitreally injected of bilateral eyes. The pars plana was vertically punctured by a 29-gauge microsyringe at 1 mm from corneal limbus and the vitreous cavity was reached. The drug liquid was then injected into the center of the vitreous cavity under direct vision and the needle was pulled out quickly after remaining for a few seconds. All above steps were conducted aseptically.

No obvious leak was observed at the injection position and ophthalmic testing confirmed that no complication such as traumatic cataract, vitreous hemorrhage, retinal hemorrhage and retinal detachment occurred. 24 hours after LPS was injected, 6 rats in each experimental group were subjected to anterior chamber puncture by 30 G needle under deep anesthesia, and then bilateral aqueous humor was collected. Other 4 rats were sacrificed by cervical dislocation and the eyeballs were taken and immobilized.

3. Determination Method 3.1 Exuded Cells Count in Aqueous Humor and Total Protein Concentration Determination The aqueous humor sample was diluted to 1:5 by trypan blue and then added into hemocytometer for manual counting under optical microscope, and total protein concentration was determined by BCA method.

3.2 Histopathologic Examination

The eyeballs were taken and immobilized by neutral formaldehyde (10%) and stored at 4° C. The sample was embedded into paraffin, cut into sagittal slices with the thickness of 5 μm, and then subjected to HE staining. The iris and ciliary body, anterior chamber, vitreous body and retina of the eyeballs were observed under optical microscope. The exuded cells in anterior chamber and vitreous cavity were counted by the same pathologist.

3.3 Statistic Analysis

The experiment date was shown as $\bar{x}\pm s$. A one-way ANOVA was used to compare the exuded cells and total protein concentration between these groups, and $P<0.05$ represents statistical significance.

4. Results 4.1 Cell Counts in Rat Aqueous Humor and Protein Concentration Determination Under LS22 Intervention.

Figure 2:
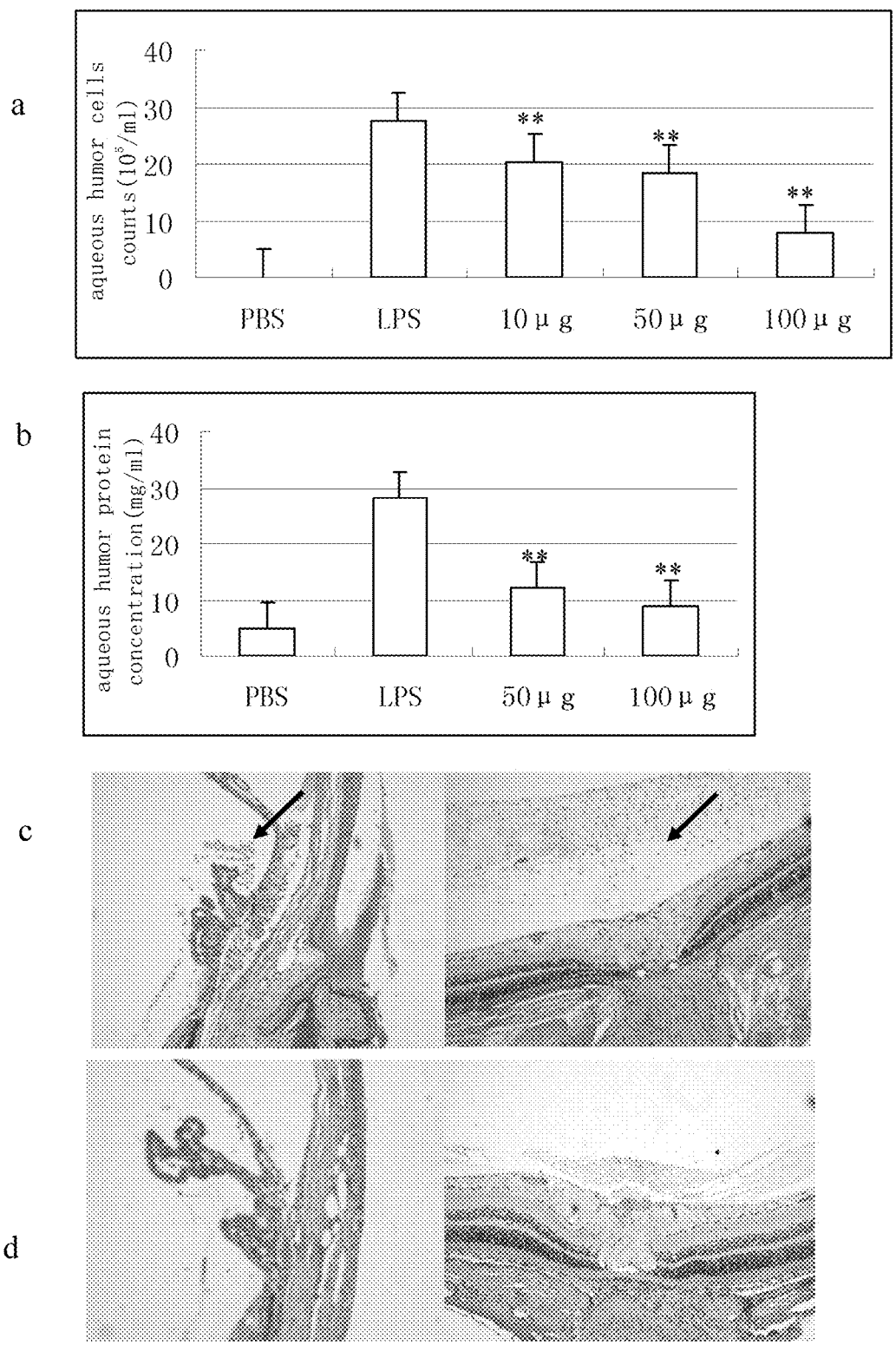
FIG. 2 shows that LS22 significantly inhibits uveitis in rats. Specifically.

Compared with the blank control group, 24 hours after LPS was injected, the exuded cells counts in rat aqueous chamber and protein concentration in aqueous humor were significantly increased, and exuded cells counts (FIG. 2a) and protein concentration in aqueous humor in LSS group were significantly reduced.

4.2 Histopathologic Examination

It was observed that there were massive amounts of cells exuded into anterior chamber, ciliary body and posterior vitreous cavity in rat eyeballs after the LPS injection. However, inflammatory cells in the tissues were significantly reduced under LS22 intervention.

The result indicated that LS22 significantly inhibited uveitis in rats.

Example 3

Effect of LS22 on LPS-Induced Mouse Macrophages Cultured In Vitro

1. Materials

Macrophages RAW264.7 of mouse were purchased from the Cell Bank of Chinese Academy of Sciences. Cell viability assay kits (MTS) were purchased from Promega, US;

Microplate Reader was purchased from Bio-Rad, US; and ELISA kits were purchased from R&D, US.

2. Cell Viability Assay

RAW264.7 cells were placed into a 96-well plate for 24-hour adherent culture, and then peptides with different concentrations were added into each well and co-cultured for another 24 hours, while no treatment was taken to the control group. 20 μl of MTS solution was added into each well after 24 hours and cultured for another 3 hours. The culture plate was taken to determine the absorbance of each well at 490 nm.

3. Determination of TNF-α and IL-6 Cytokine Level in Cell Supernatant

Mouse RAW264.7 cells were inoculated on the 24-well cell culture plate (400 μl/well). RAW264.7 was pretreated with 0.1-10 μM of LS22 for 30 min, and then LPS (100 ng/mL) was added and co-incubated for 24 hours. Cell supernatant in each well was collected and TNF-α and IL-6 level was determined by ELISA kits.

4. Statistic Analysis

The experiment date was shown as x̄±s. A SPSS 11.0 statistical package was used for statistic analysis and a one-way ANOVA was used to compare RAW264.7 cell viability results, TNF-α and IL-6 level between the groups, and P<0.05 represents statistical significance.

5. Results 5.1 Cell Viability Assay Under LS22 Intervention

After the RAW264.7 cells were co-incubated with LS22 for 24 hours, there is no statistically significant difference in cell viability compared with the control group, and no toxicity was observed to the cells.

5.2 LS22 Inhibited TNF-α and IL-6 Expression Induced by LPS in RAW264.7 Cells

Figure 3:
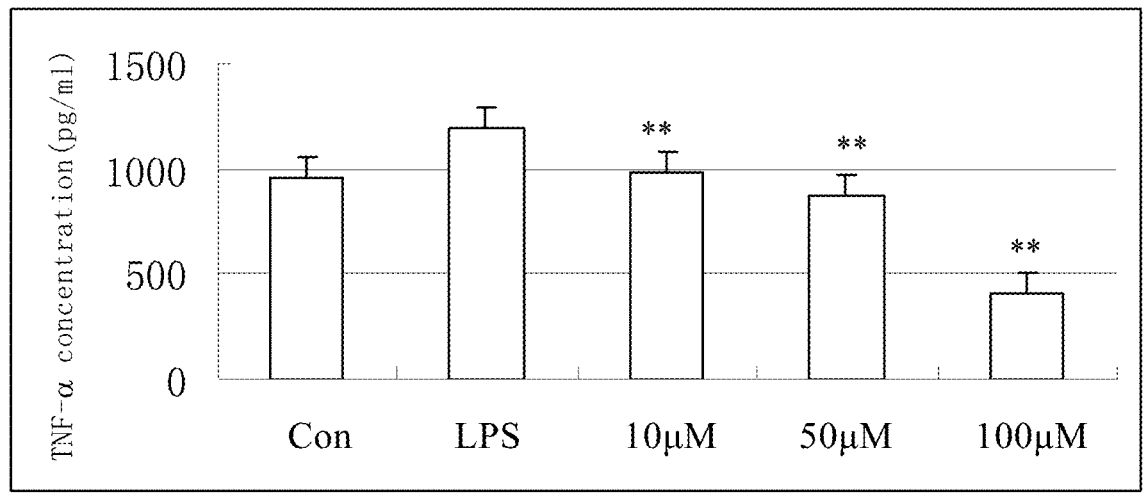
FIG. 3 shows the resulting effects of LS22 on TNF-α and IL-6 expression. Specifically.
Figure 3:
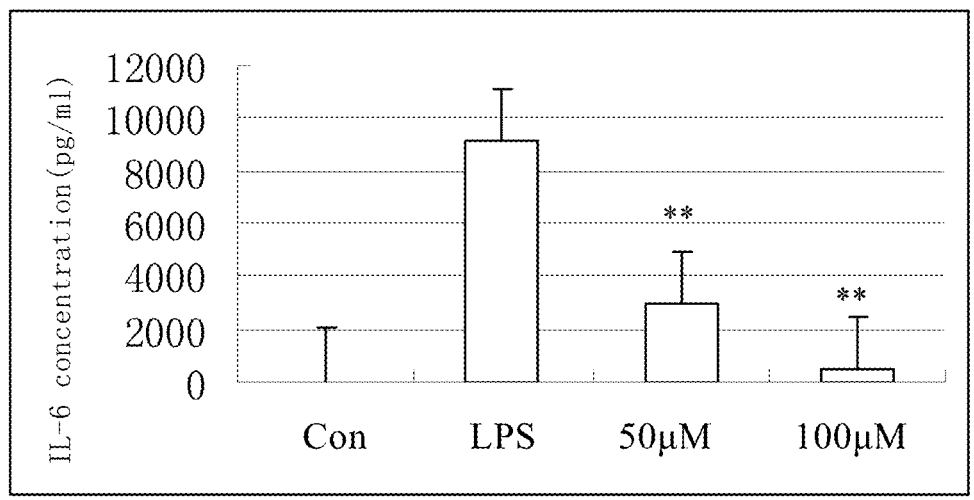

TNF-α and IL-6 level in the supernatant of RAW264.7 cells in LPS group was remarkably increased while LPS-induced TNF-α (FIG. 3a) and IL-6 (FIG. 3b) level was remarkably inhibited in LS22 group.

Example 4

Preparation of Eyedrop

The following components were mixed via conventional techniques to obtain a 1% eyedrop, the formulation of which was as follows:

| | |
|---|---|
| LS peptide | 10 mg |
| Hydroxylpropyl methyl cellulose | 0.03 g |
| Sterile water | q.s. to 10 ml |

The osmotic pressure was adjusted to 300 Osm, and the pH was adjusted to 6.8-7.1.

Five volunteers used the eyedrop for one week, three times per day, and 1 drop/eye for each time. The results showed that the eyedrop could inhibit ocular inflammation.

Example 5

Preparation and Activity of Other Derived Polypeptides

Derived Polypeptides were prepared as follows. Polypeptides were prepared according to the method in Example 1, and the inhibiting effect of the polypeptides on ocular inflammation was determined according to Examples 2-3. The results are shown as follows:

Polypeptide 1: the sequence was the same as SEQ ID NO.: 1 except that Ile in Xaa8 was substituted by Leu;

Polypeptide 2: the sequence was the same as SEQ ID NO.: 1 except that Gln in Xaa10 was substituted by Asn;

Polypeptide 3: the sequence was the same as SEQ ID NO.: 1 except that Ser in Xaa12 was substituted by Thr;

Polypeptide 4: the sequence was the same as SEQ ID NO.: 1 except that Tyr in Xaa15 was substituted by Trp;

Polypeptide 5: the sequence was the same as SEQ ID NO.: 1 except that Xaa23 was Arg;

Polypeptide 6: the sequence was as set forth by SEQ ID NO.: 3;

Polypeptide 7: the sequence was as set forth by SEQ ID NO.: 5;

The results indicated that in the treatment group of the above derived polypeptides 1-6 (10 μg group or 10 μM), TNF-α and IL-6 level induced by LPS was significantly inhibited and the anti-inflammation effect is obvious. Further, polypeptide 7 exhibits an anti-inflammation effect to some extent, but the effect is weaker than LS22 (about 30%).

Example 6

Polypeptides 8-23 were prepared according to the method in Example 1.

Example 7

Levels of TNF-a and IL-6 in LPS-stimulated RAW264.7 cells were cultured in 24-well plates and starved in serum-free DMEM for 24 h. Then, the cells were treated with LS22-peptide-series at various concentrations (50 uM) for 30 min preceding the addition of LPS (100 ng/ml). The expression of TNF-a and IL-6 in the culture medium 24 h after LPS stimulation was assessed using ELISA kits (R&D).

Figure 4:
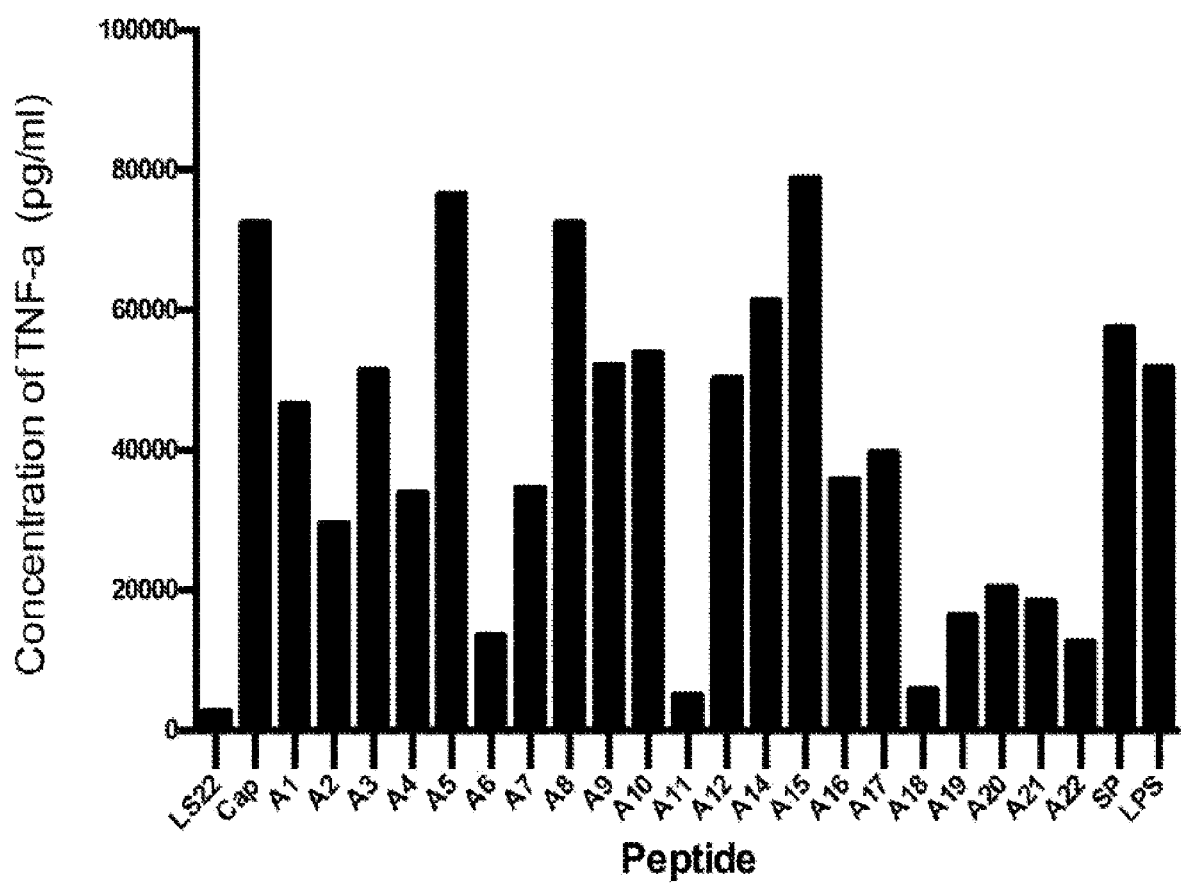
FIG. 4 shows the level of TNF-α expression.
Figure 5:
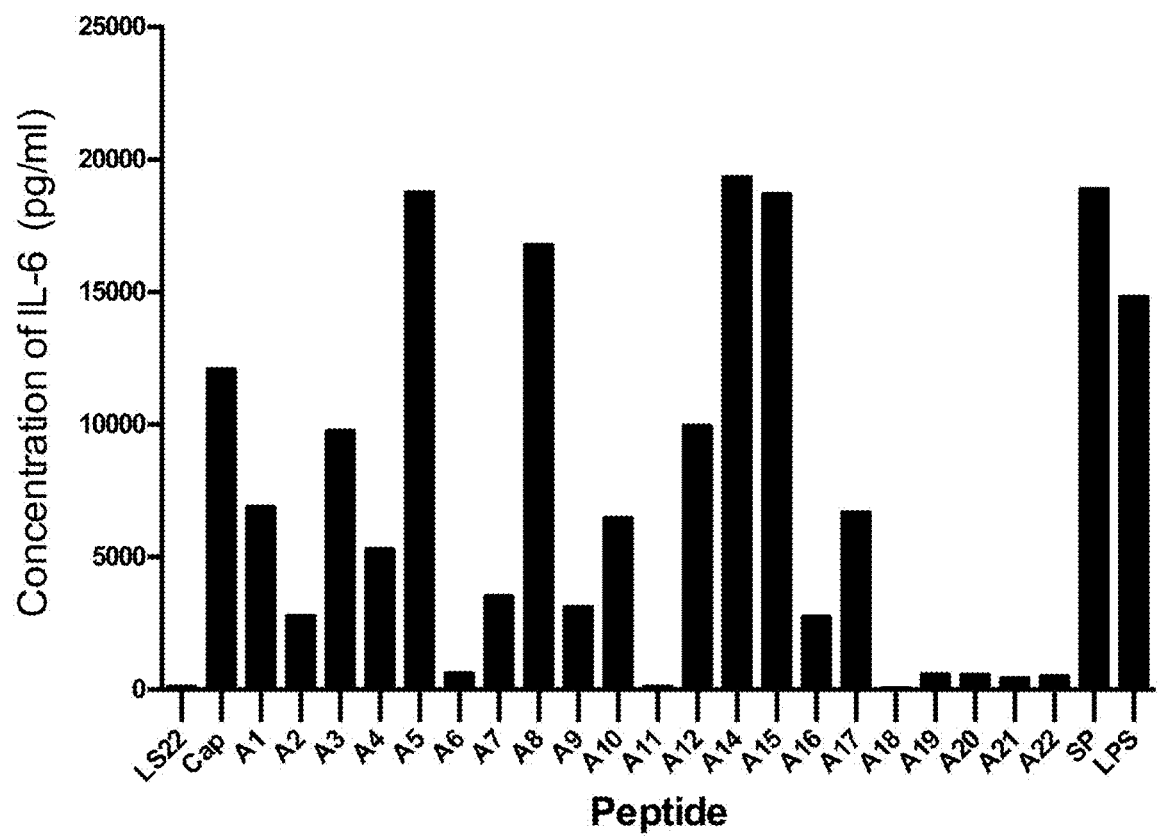
FIG. 5 shows the level of IL-6 expression.

The results are shown in FIGS. 4 and 5. The sequences of peptides are shown in table II.

| Name | Sequence |
|---|---|
| LS22 | LDLSHNSISQESALYLLETLPS |
| cap | Ac-LDLSHNSISQESALYLLETLPS-NH2 |
| A1 | ADLSHNSISQESALYLLETLPS |
| A2 | LALSHNSISQESALYLLETLPS |
| A3 | LDASHNSISQESALYLLETLPS |
| A4 | LDLAHNSISQESALYLLETLPS |
| A6 | LDLSHASISQESALYLLETLPS |
| A7 | LDLSHNAISQESALYLLETLPS |
| A8 | LDLSHNSASQESALYLLETLPS |
| A9 | LDLSHNSIAQESALYLLETLPS |
| A10 | LDLSHNSISAESALYLLETLPS |
| A11 | LDLSHNSISQASALYLLETLPS |
| A12 | LDLSHNSISQEAALYLLETLPS |
| A14 | LDLSHNSISQESAAYLLETLPS |
| A15 | LDLSHNSISQESALALLETLPS |

| Name | Sequence |
|---|---|
| A16 | LDLSHNSISQESALYAlETLPS |
| A17 | LDLSHNSISQESALYLAETLPS |
| A18 | LDLSHNSISQESALYLLATLPS |
| A19 | LDLSHNSISQESALYLLEALPS |
| A20 | LDLSHNSISQESALYLLETAPS |
| A21 | LDLSHNSISQESALYLLETLAS |
| A22 | LDLSHNSISQESALYLLETLPA |
| SP (Scramble peptide) | DSHILNQESAYLLSESLLSTPL |

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

The invention claimed is:

1. A polypeptide consisting of the amino acid sequence of Formula I, or a pharmaceutically acceptable salt thereof

[Xaa0]-[Xaa1]-[Xaa2]-[Xaa3]-[Xaa4]-[Xaa5]-[Xaa6]- (I)

[Xaa7]-[Xaa8]-[Xaa9]-[Xaa10]-[Xaa11]-[Xaa12]-

[Xaa13]-[Xaa14]-[Xaa15]-[Xaa16]-[Xaa17]-

[Xaa18]-[Xaa19]-[Xaa20]-[Xaa21]-[Xaa22]-[Xaa23]

wherein,
Xaa0 is absent, or a peptide segment consisting of 1-3 amino acids;
Xaa1 is selected from the group consisting of Leu, Ile, Val, and Ala;
Xaa2 is selected from the group consisting of Asp and Ala;
Xaa3 is selected from the group consisting of Leu, Ile, Val, and Ala;
Xaa4 is selected from the group consisting of Ser, Thr, and Ala;
Xaa5 is selected from the group consisting of His and Arg;
Xaa6 is selected from the group consisting of Asn, Gln, and Ala;
Xaa7 is selected from the group consisting of Ser, Thr, and Ala;
Xaa8 is selected from the group consisting of Ile and Leu;
Xaa9 is selected from the group consisting of Ser, Thr, and Ala;
Xaa10 is selected from the group consisting of Gln and Asn;
Xaa11 is selected from the group consisting of Glu, Asp, and Ala;
Xaa12 is selected from the group consisting of Ser, Thr, and Ala;
Xaa13 is selected from the group consisting of Ala, Val, Leu, and Ile;
Xaa14 is selected from the group consisting of Leu, Ile, Val, Met, Ala, and Phe;
Xaa15 is selected from the group consisting of Tyr, Trp, and Phe;
Xaa16 is selected from the group consisting of Leu, Ile, Val, and Ala;
Xaa17 is selected from the group consisting of Leu, Ile, Val, and Ala;
Xaa18 is selected from the group consisting of Glu, Asp, Ala, Val, and Ile;
Xaa19 is selected from the group consisting of Thr, Ser, and Ala;
Xaa20 is selected from the group consisting of Leu, Ile, Val, and Ala;
Xaa21 is selected from the group consisting of Pro and Ala;

Xaa22 is selected from the group consisting of Ser, Thr, and Ala;

Xaa23 is absent, or a peptide segment consisting of 1-3 amino acids;

and the polypeptide exhibits an activity of inhibiting inflammation, wherein the polypeptide is selected from the group consisting of SEQ ID NO: 11, 12, 13, 14, 15, 16, 17, 18, 19, 20, 21, 22, 23, 24, 25, and 26.

2. An isolated nucleic acid molecule encoding the polypeptide according to claim 1.

3. A pharmaceutical composition comprising:
 (a) the polypeptide according to claim 1 or a pharmaceutically acceptable salt thereof; and
 (b) a pharmaceutically acceptable carrier or excipient.

4. The pharmaceutical composition according to claim 3, wherein said composition is in the form of eyedrop, injection, or eye ointment.

5. A method for inhibiting inflammation caused by TNF-α and/or IL-6 in a mammal, comprising administering the polypeptide or the pharmaceutically acceptable salt thereof according to claim 1 to a subject in need thereof.

6. A method for preparing a pharmaceutical composition, comprising mixing the polypeptide or the pharmaceutically acceptable salt thereof according to claim 1 with a pharmaceutically acceptable carrier or excipient, thereby obtaining the pharmaceutical composition.

7. The method according to claim 5, wherein the inflammation is uveitis.

\* \* \* \* \*

SEQUENCE LISTING

<160> NUMBER OF SEQ ID NOS: 31

<210> SEQ ID NO 1
<211> LENGTH: 22
<212> TYPE: PRT
<213> ORGANISM: artificial sequence
<220> FEATURE:
<223> OTHER INFORMATION: synthesized polypeptide

<400> SEQUENCE: 1

Leu Asp Leu Ser His Asn Ser Ile Ser Gln Glu Ser Ala Leu Tyr Leu
1               5                   10                  15

Leu Glu Thr Leu Pro Ser
            20

<210> SEQ ID NO 2
<211> LENGTH: 66
<212> TYPE: DNA
<213> ORGANISM: Artificial sequence
<220> FEATURE:
<223> OTHER INFORMATION: synthesized nucleotide

<400> SEQUENCE: 2
cttgatctga gtcacaacag catttctcag gaaagtgccc tgtacctgct ggagacactg     60
ccctcc                                                               66

<210> SEQ ID NO 3
<211> LENGTH: 22
<212> TYPE: PRT
<213> ORGANISM: Artificial sequence
<220> FEATURE:
<223> OTHER INFORMATION: synthesized polypeptide

<400> SEQUENCE: 3

Leu Cys Leu Ser Glu Cys Pro Leu Glu Pro Pro Ser Leu Thr Arg Leu
1               5                   10                  15

Cys Ala Thr Leu Lys Asp
            20

<210> SEQ ID NO 4
<211> LENGTH: 66
<212> TYPE: DNA
<213> ORGANISM: Artificial sequence
<220> FEATURE:
<223> OTHER INFORMATION: synthesized nucleotide

<400> SEQUENCE: 4
ctctgcctca gtgagtgtcc tctggagccc ccaagcctca cccgcctctg tgccactctg    60
aaggac    66

<210> SEQ ID NO 5
<211> LENGTH: 21
<212> TYPE: PRT
<213> ORGANISM: Artificial sequence
<220> FEATURE:
<223> OTHER INFORMATION: synthesized polypeptide

<400> SEQUENCE: 5

Ala Leu Gln Ser Leu Asn Leu Ser Glu Asn Gly Leu Ser Leu Asp Ala
1               5                   10                  15

Val Leu Gly Leu Val
            20

<210> SEQ ID NO 6
<211> LENGTH: 22
<212> TYPE: PRT
<213> ORGANISM: artificial sequence
<220> FEATURE:
<223> OTHER INFORMATION: peptide 1

<400> SEQUENCE: 6

Leu Asp Leu Ser His Asn Ser Leu Ser Gln Glu Ser Ala Leu Tyr Leu
1               5                   10                  15

Leu Glu Thr Leu Pro Ser
            20

<210> SEQ ID NO 7
<211> LENGTH: 22
<212> TYPE: PRT
<213> ORGANISM: artificial sequence
<220> FEATURE:
<223> OTHER INFORMATION: peptide 2

<400> SEQUENCE: 7

Leu Asp Leu Ser His Asn Ser Ile Ser Asn Glu Ser Ala Leu Tyr Leu
1               5                   10                  15

Leu Glu Thr Leu Pro Ser
            20

<210> SEQ ID NO 8
<211> LENGTH: 22
<212> TYPE: PRT
<213> ORGANISM: artificial sequence
<220> FEATURE:
<223> OTHER INFORMATION: peptide 3

<400> SEQUENCE: 8

Leu Asp Leu Ser His Asn Ser Ile Ser Gln Glu Thr Ala Leu Tyr Leu
1               5                   10                  15

Leu Glu Thr Leu Pro Ser
            20

<210> SEQ ID NO 9
<211> LENGTH: 22
<212> TYPE: PRT
<213> ORGANISM: artificial sequence
<220> FEATURE:
<223> OTHER INFORMATION: peptide 4

```
<400> SEQUENCE: 9

Leu Asp Leu Ser His Asn Ser Ile Ser Gln Glu Ser Ala Leu Trp Leu
1               5                   10                  15

Leu Glu Thr Leu Pro Ser
            20

<210> SEQ ID NO 10
<211> LENGTH: 23
<212> TYPE: PRT
<213> ORGANISM: artificial sequence
<220> FEATURE:
<223> OTHER INFORMATION: peptide 5

<400> SEQUENCE: 10

Leu Asp Leu Ser His Asn Ser Ile Ser Gln Glu Ser Ala Leu Tyr Leu
1               5                   10                  15

Leu Glu Thr Leu Pro Ser Arg
            20

<210> SEQ ID NO 11
<211> LENGTH: 22
<212> TYPE: PRT
<213> ORGANISM: artificial sequence
<220> FEATURE:
<223> OTHER INFORMATION: peptide 8

<400> SEQUENCE: 11

Leu Asp Leu Ser His Ala Ser Ile Ser Gln Glu Ser Ala Leu Tyr Leu
1               5                   10                  15

Leu Glu Thr Leu Pro Ser
            20

<210> SEQ ID NO 12
<211> LENGTH: 22
<212> TYPE: PRT
<213> ORGANISM: artificial sequence
<220> FEATURE:
<223> OTHER INFORMATION: peptide 9

<400> SEQUENCE: 12

Leu Asp Leu Ser His Asn Ser Ile Ser Gln Ala Ser Ala Leu Tyr Leu
1               5                   10                  15

Leu Glu Thr Leu Pro Ser
            20

<210> SEQ ID NO 13
<211> LENGTH: 22
<212> TYPE: PRT
<213> ORGANISM: artificial sequence
<220> FEATURE:
<223> OTHER INFORMATION: peptide 10

<400> SEQUENCE: 13

Leu Asp Leu Ser His Asn Ser Ile Ser Gln Glu Ser Ala Leu Tyr Leu
1               5                   10                  15

Leu Ala Thr Leu Pro Ser
            20

<210> SEQ ID NO 14
<211> LENGTH: 22
<212> TYPE: PRT
<213> ORGANISM: artificial sequence
<220> FEATURE:
<223> OTHER INFORMATION: peptide 11
```

```
<400> SEQUENCE: 14

Leu Asp Leu Ser His Asn Ser Ile Ser Gln Glu Ser Ala Leu Tyr Leu
1               5                   10                  15

Leu Glu Ala Leu Pro Ser
            20

<210> SEQ ID NO 15
<211> LENGTH: 22
<212> TYPE: PRT
<213> ORGANISM: artificial sequence
<220> FEATURE:
<223> OTHER INFORMATION: peptide 12

<400> SEQUENCE: 15

Leu Asp Leu Ser His Asn Ser Ile Ser Gln Glu Ser Ala Leu Tyr Leu
1               5                   10                  15

Leu Glu Thr Ala Pro Ser
            20

<210> SEQ ID NO 16
<211> LENGTH: 22
<212> TYPE: PRT
<213> ORGANISM: artificial sequence
<220> FEATURE:
<223> OTHER INFORMATION: peptide 13

<400> SEQUENCE: 16

Leu Asp Leu Ser His Asn Ser Ile Ser Gln Glu Ser Ala Leu Tyr Leu
1               5                   10                  15

Leu Glu Thr Leu Ala Ser
            20

<210> SEQ ID NO 17
<211> LENGTH: 22
<212> TYPE: PRT
<213> ORGANISM: artificial sequence
<220> FEATURE:
<223> OTHER INFORMATION: peptide 14

<400> SEQUENCE: 17

Leu Asp Leu Ser His Asn Ser Ile Ser Gln Glu Ser Ala Leu Tyr Leu
1               5                   10                  15

Leu Glu Thr Leu Pro Ala
            20

<210> SEQ ID NO 18
<211> LENGTH: 22
<212> TYPE: PRT
<213> ORGANISM: artificial sequence
<220> FEATURE:
<223> OTHER INFORMATION: peptide 15

<400> SEQUENCE: 18

Ala Asp Leu Ser His Asn Ser Ile Ser Gln Glu Ser Ala Leu Tyr Leu
1               5                   10                  15

Leu Glu Thr Leu Pro Ser
            20

<210> SEQ ID NO 19
<211> LENGTH: 22
<212> TYPE: PRT
<213> ORGANISM: artificial sequence
<220> FEATURE:
```

```
<223> OTHER INFORMATION: peptide 16

<400> SEQUENCE: 19

Leu Ala Leu Ser His Asn Ser Ile Ser Gln Glu Ser Ala Leu Tyr Leu
1               5                   10                  15

Leu Glu Thr Leu Pro Ser
            20

<210> SEQ ID NO 20
<211> LENGTH: 22
<212> TYPE: PRT
<213> ORGANISM: artificial sequence
<220> FEATURE:
<223> OTHER INFORMATION: peptide 17

<400> SEQUENCE: 20

Leu Asp Ala Ser His Asn Ser Ile Ser Gln Glu Ser Ala Leu Tyr Leu
1               5                   10                  15

Leu Glu Thr Leu Pro Ser
            20

<210> SEQ ID NO 21
<211> LENGTH: 22
<212> TYPE: PRT
<213> ORGANISM: artificial sequence
<220> FEATURE:
<223> OTHER INFORMATION: peptide 18

<400> SEQUENCE: 21

Leu Asp Leu Ala His Asn Ser Ile Ser Gln Glu Ser Ala Leu Tyr Leu
1               5                   10                  15

Leu Glu Thr Leu Pro Ser
            20

<210> SEQ ID NO 22
<211> LENGTH: 22
<212> TYPE: PRT
<213> ORGANISM: artificial sequence
<220> FEATURE:
<223> OTHER INFORMATION: peptide 19

<400> SEQUENCE: 22

Leu Asp Leu Ser His Asn Ala Ile Ser Gln Glu Ser Ala Leu Tyr Leu
1               5                   10                  15

Leu Glu Thr Leu Pro Ser
            20

<210> SEQ ID NO 23
<211> LENGTH: 22
<212> TYPE: PRT
<213> ORGANISM: artificial sequence
<220> FEATURE:
<223> OTHER INFORMATION: peptide 20

<400> SEQUENCE: 23

Leu Asp Leu Ser His Asn Ser Ile Ala Gln Glu Ser Ala Leu Tyr Leu
1               5                   10                  15

Leu Glu Thr Leu Pro Ser
            20

<210> SEQ ID NO 24
<211> LENGTH: 22
<212> TYPE: PRT
<213> ORGANISM: artificial sequence
```

```
<220> FEATURE:
<223> OTHER INFORMATION: peptide 21

<400> SEQUENCE: 24

Leu Asp Leu Ser His Asn Ser Ile Ser Gln Glu Ala Ala Leu Tyr Leu
1               5                   10                  15

Leu Glu Thr Leu Pro Ser
            20

<210> SEQ ID NO 25
<211> LENGTH: 22
<212> TYPE: PRT
<213> ORGANISM: artificial sequence
<220> FEATURE:
<223> OTHER INFORMATION: peptide 22

<400> SEQUENCE: 25

Leu Asp Leu Ser His Asn Ser Ile Ser Gln Glu Ser Ala Leu Tyr Ala
1               5                   10                  15

Leu Glu Thr Leu Pro Ser
            20

<210> SEQ ID NO 26
<211> LENGTH: 22
<212> TYPE: PRT
<213> ORGANISM: artificial sequence
<220> FEATURE:
<223> OTHER INFORMATION: peptide 23

<400> SEQUENCE: 26

Leu Asp Leu Ser His Asn Ser Ile Ser Gln Glu Ser Ala Leu Tyr Leu
1               5                   10                  15

Ala Glu Thr Leu Pro Ser
            20

<210> SEQ ID NO 27
<211> LENGTH: 22
<212> TYPE: PRT
<213> ORGANISM: artificial sequence
<220> FEATURE:
<223> OTHER INFORMATION: synthesized polypeptide

<400> SEQUENCE: 27

Leu Asp Leu Ser His Asn Ser Ala Ser Gln Glu Ser Ala Leu Tyr Leu
1               5                   10                  15

Leu Glu Thr Leu Pro Ser
            20

<210> SEQ ID NO 28
<211> LENGTH: 22
<212> TYPE: PRT
<213> ORGANISM: artificial sequence
<220> FEATURE:
<223> OTHER INFORMATION: synthesized polypeptide

<400> SEQUENCE: 28

Leu Asp Leu Ser His Asn Ser Ile Ser Ala Glu Ser Ala Leu Tyr Leu
1               5                   10                  15

Leu Glu Thr Leu Pro Ser
            20

<210> SEQ ID NO 29
<211> LENGTH: 22
<212> TYPE: PRT
```

```
<213> ORGANISM: artificial sequence
<220> FEATURE:
<223> OTHER INFORMATION: synthesized polypeptide

<400> SEQUENCE: 29

Leu Asp Leu Ser His Asn Ser Ile Ser Gln Glu Ser Ala Ala Tyr Leu
1               5                   10                  15

Leu Glu Thr Leu Pro Ser
            20

<210> SEQ ID NO 30
<211> LENGTH: 22
<212> TYPE: PRT
<213> ORGANISM: artificial sequence
<220> FEATURE:
<223> OTHER INFORMATION: synthesized polypeptide

<400> SEQUENCE: 30

Leu Asp Leu Ser His Asn Ser Ile Ser Gln Glu Ser Ala Leu Ala Leu
1               5                   10                  15

Leu Glu Thr Leu Pro Ser
            20

<210> SEQ ID NO 31
<211> LENGTH: 22
<212> TYPE: PRT
<213> ORGANISM: artificial sequence
<220> FEATURE:
<223> OTHER INFORMATION: synthesized polypeptide

<400> SEQUENCE: 31

Asp Ser His Ile Leu Asn Gln Glu Ser Ala Tyr Leu Leu Ser Glu Ser
1               5                   10                  15

Leu Leu Ser Thr Pro Leu
            20
```